(12) United States Patent
Dombrowsky et al.

(10) Patent No.: US 9,198,991 B2
(45) Date of Patent: Dec. 1, 2015

(54) APPARATUS FOR DESTROYING PATHOGENS ASSOCIATED WITH FOOTWEAR

(71) Applicant: Sole Sanitizer, Inc., Oyster Bay, NY (US)

(72) Inventors: Rachel Dombrowsky, Hewlett, NY (US); Jason Pileggi, Bayville, NY (US); Eugene Pileggi, Bayville, NY (US)

(73) Assignee: Sole Sanitizer, Inc., Oyster Bay, NY (US)

(*) Notice: Subject to any disclaimer, the term of this patent is extended or adjusted under 35 U.S.C. 154(b) by 0 days.

(21) Appl. No.: 14/542,047

(22) Filed: Nov. 14, 2014

(65) Prior Publication Data

US 2015/0132183 A1    May 14, 2015

Related U.S. Application Data

(60) Provisional application No. 61/904,056, filed on Nov. 14, 2013.

(51) Int. Cl.
*A61N 5/00* (2006.01)
*A61L 2/00* (2006.01)
*A61L 2/10* (2006.01)

(52) U.S. Cl.
CPC .......................... *A61L 2/10* (2013.01)

(58) Field of Classification Search
CPC ............................................ A61L 2/10
USPC .......................................... 422/24; 250/492.1
See application file for complete search history.

(56) References Cited

U.S. PATENT DOCUMENTS

| | | |
|---|---|---|
| 7,875,869 B1 | 1/2011 | Shadan |
| 8,277,741 B2 | 10/2012 | McCabe |
| 8,624,202 B2 | 1/2014 | Gil |
| 2008/0310996 A1* | 12/2008 | Kim et al. ............ 422/24 |
| 2009/0004047 A1* | 1/2009 | Hunter et al. ......... 422/4 |
| 2009/0314308 A1* | 12/2009 | Kim et al. ............ 134/1 |
| 2010/0193709 A1 | 8/2010 | Dalton |
| 2012/0167325 A1 | 7/2012 | Omidi |
| 2013/0101461 A1* | 4/2013 | Gil et al. ............ 422/24 |

FOREIGN PATENT DOCUMENTS

EP    1223989 A1    7/2002

OTHER PUBLICATIONS

PCT International Search Report and Written Opinion for PCT/US2014/065766 dated Feb. 26, 2015.

* cited by examiner

*Primary Examiner* — Kevin Joyner
(74) *Attorney, Agent, or Firm* — Carter, DeLuca, Farrell & Schmidt, LLP

(57) ABSTRACT

An apparatus for destroying microorganisms includes a housing, a platform, a reflective tray, and a source of ultraviolet light. The platform is supported on the housing and is configured to permit passage of ultraviolet light at an angle therethrough. The reflective tray is disposed within the housing. The source of ultraviolet light is disposed adjacent the reflective tray such that the reflective tray directs ultraviolet light emitted by the source of ultraviolet light through the platform.

37 Claims, 7 Drawing Sheets

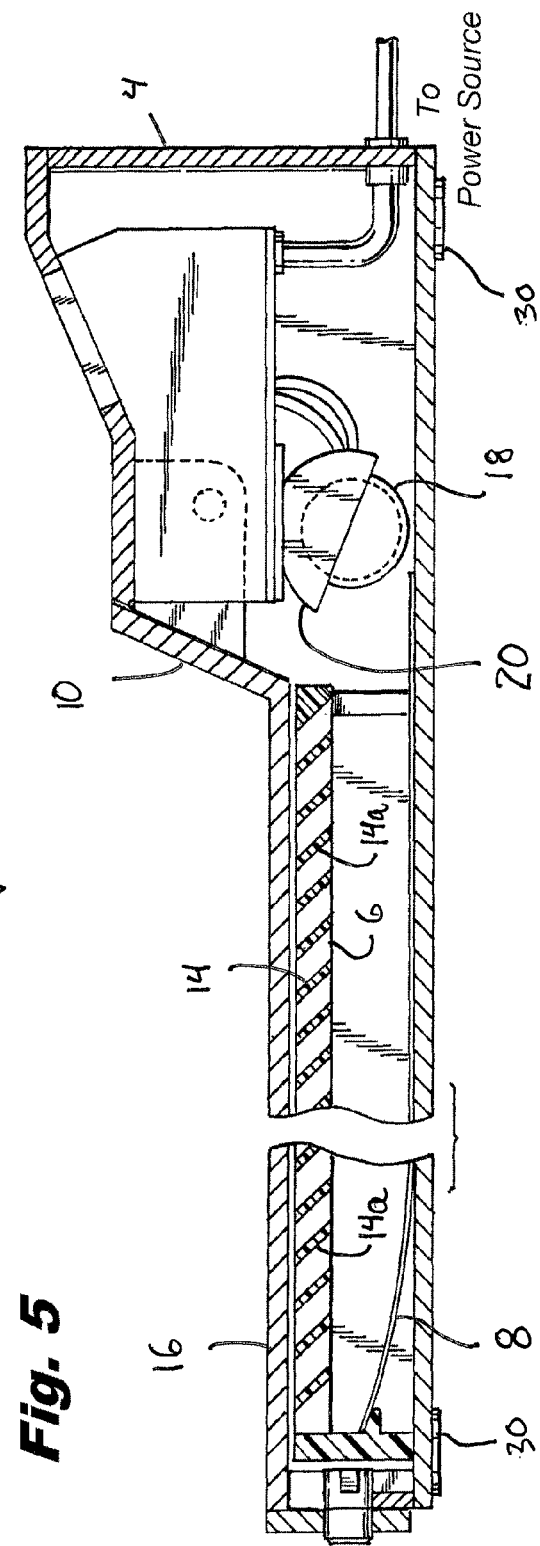
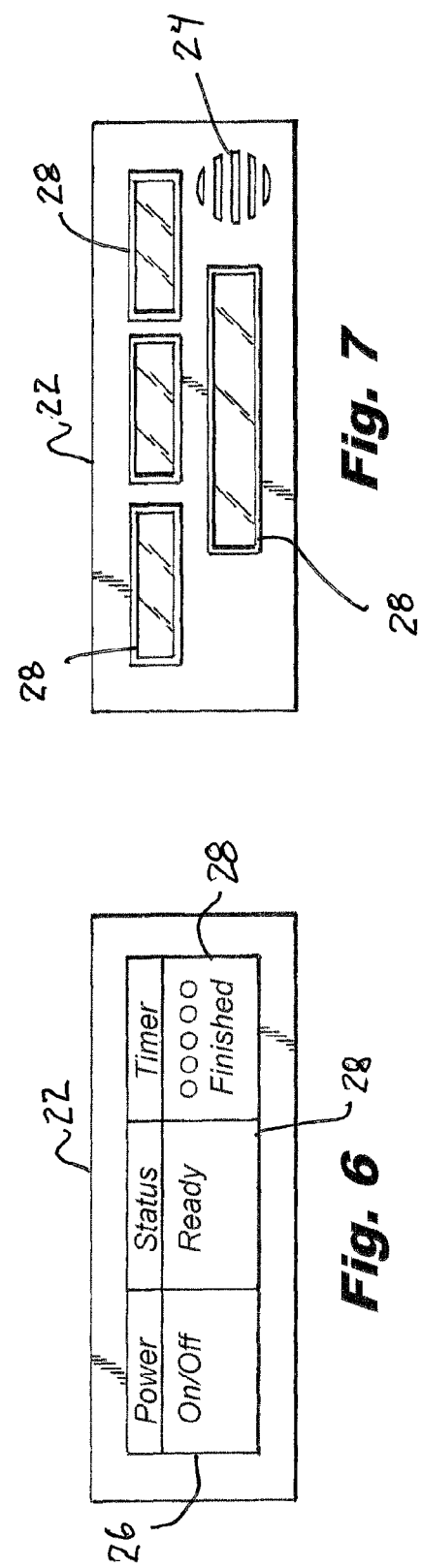
Fig. 5
Fig. 6
Fig. 7

APPARATUS FOR DESTROYING PATHOGENS ASSOCIATED WITH FOOTWEAR

CROSS-REFERENCE TO RELATED APPLICATIONS

This application claims the benefit of and priority to U.S. Provisional Patent Application Ser. No. 61/904,056, filed on Nov. 14, 2013, the entire contents of which are incorporated by reference herein.

BACKGROUND

1. Technical Field

The present disclosure relates to devices for cleaning footwear. More specifically, the present disclosure relates to an apparatus that uses ultraviolet light to destroy or inhibit the growth of surface pathogens, such as, for example, virus, bacteria, mold, spore, and fungi, and/or to reduce chemical contaminants.

2. Background of Related Art

People are a primary vehicle for pathogens entering homes and healthcare facilities. The pathogens can cause sickness, disease and possible death. To help combat this problem, hand washing and hand sanitizers have been widely adopted. Unfortunately, nothing has been implemented with widespread use to combat the pathogens that enter homes and facilities on the soles of people's footwear.

Door mats, the primary means for cleaning shoe bottoms, remove dirt but not pathogens, and can quickly become an incubator of germs. Other solutions such as liquid dips are not practical for high traffic areas and require frequent maintenance to stay effective. Disposable booties or shoe covers are used in professional environments but do not work well in public areas, as people tend to be self-conscience about wearing them, and there are safety concerns over people tripping while wearing such covers.

Other attempted solutions are difficult to implement, expose people to UV-C light, and/or are deficient in killing pathogens.

SUMMARY

In one aspect of the present disclosure, an apparatus for destroying pathogens is provided. The apparatus includes a housing, a platform, a reflective tray, and a source of ultraviolet light. The platform is supported on the housing and is configured to permit passage of ultraviolet light at an angle therethrough. The reflective tray is disposed within the housing. The source of ultraviolet light is disposed adjacent the reflective tray such that the reflective tray directs ultraviolet light emitted by the source of ultraviolet light through the platform.

In some embodiments, the platform may have a plurality of spaced apart transverse bars. Each bar may be angled relative to a transverse axis defined by the platform such that the ultraviolet light passes through spaces defined between adjacent bars at a non-perpendicular angle relative to a plane defined by the platform. Each bar may be angled in a direction from a top surface of the platform to a bottom surface of the platform such that the ultraviolet light is directed away from the front end of the housing.

It is contemplated that the spaces may each define an axis extending at an angle. The angle may be between 1 and 90 degrees relative to the plane of the platform.

It is envisioned that the platform may further include a plurality of spaced apart longitudinal bars in a crisscrossing arrangement with the plurality of spaced apart transverse bars. The transverse bars and the longitudinal bars may together define a plurality of openings. The openings located adjacent a rear end of the platform may be smaller in dimension than the openings located adjacent a front end of the platform.

In some aspects, the platform may be fabricated from aluminum.

In some embodiments, the apparatus may further include a cover attached to the housing and configured to selectively cover the platform.

It is contemplated that the reflective tray may be fabricated from a plastic material having a reflective white polytetrafluoroethylene coating.

It is envisioned that the reflective tray may have a first end and a second end. The first end may be disposed adjacent the source of ultraviolet light, and the second end may be disposed adjacent a rear end of the housing. The second end of the reflective tray may be angled relative to the first end of the reflective tray in a direction toward the platform.

In some aspects, the source of ultraviolet light may be an ultraviolet bulb that emits short-wavelength ultraviolet radiation (UV-C light). The ultraviolet bulb may be disposed within the housing at a front end of the housing. The apparatus may further include a reflector disposed on the ultraviolet light bulb. The reflector is configured to direct ultraviolet light emitted by the ultraviolet bulb toward the reflective tray.

In some embodiments, the apparatus may further include a mat positionable on the platform. The mat may have a pair of cutouts formed through a thickness thereof that have an oblong configuration. The mat may be configured to allow passage of ultraviolet light only through the pair of cutouts. It is contemplated that the mat may be fixed to the platform or removable from the platform.

It is contemplated that the apparatus may further include a strain gauge configured to sense a weight of a person standing on the platform.

It is envisioned that the apparatus may further include an ozone generator disposed within the housing between a base of the housing and the reflective tray. The reflective tray may be perforated to allow passage of ozone gas emitted by the ozone generator.

In another aspect of the present disclosure, a method of sanitizing footwear is provided. The method includes positioning footwear on the platform of the apparatus and emitting, from the source of ultraviolet light, ultraviolet light. The ultraviolet light contacts the reflective tray thereby directing the ultraviolet light through the platform, at an angle, and into contact with the footwear.

In some embodiments, the method may further include passing the ultraviolet light through the spaces defined through the platform at a non-perpendicular angle relative to the plane defined by the platform.

It is contemplated that the method may further include directing the ultraviolet light away from the front end of the housing.

It is an object of the present disclosure to provide a shoe sanitizer which effectively and efficiently sanitizes the soles of shoes.

It is another object of the present disclosure to provide a shoe sanitizer, which allows home owners or healthcare facilities the peace of mind that 99% of the germs carried on shoe soles will be eradicated.

It is still another objection of the present disclosure to provide a shoe sanitizer that does not require the user thereof to remove his shoes.

It is a further object of the present disclosure to provide a shoe sanitizer that is easy to use and involves a simple process for sanitizing one's shoes.

It is yet a further object of the present disclosure to provide a shoe sanitizer that can support a high throughput of users.

It is still another object of the present disclosure to provide a shoe sanitizer that is effective in killing most pathogens carried on the soles of a user's shoes.

It is yet another object of the present disclosure to provide a shoe sanitizer that addresses certain safety concerns over the use of UV-C light.

It is a further object of the present disclosure to provide a shoe sanitizer that requires limited and simple maintenance.

It is yet a further object of the present disclosure to provide a shoe sanitizer that overcomes the inherent disadvantages of known shoe sanitizing apparatus.

A shoe sanitizer constructed in accordance with one form of the present disclosure includes a stand-on enclosure which houses an ultraviolet light source. A user stands on top of the housing, which is similar in size to a conventional personal weighing scale. The user may wear his shoes while standing on the shoe sanitizer of the present disclosure. Ultraviolent light, and in particular, UV-C light rays, are reflected onto the soles of the user's shoes at a particular angle and for a predetermined period of time, killing the pathogens thereon and leaving the shoes essentially free of contaminants.

Further details, advantages, and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein:

FIG. 5 is a cross-sectional view of the apparatus of the present disclosure taken along line 5-5 of FIG. 2;

FIG. 6 is a front view of a display of the apparatus of FIG. 1;

FIG. 7 is a front view of another embodiment of a display of the apparatus of FIG. 1;

DETAILED DESCRIPTION

Figures 1, 2:
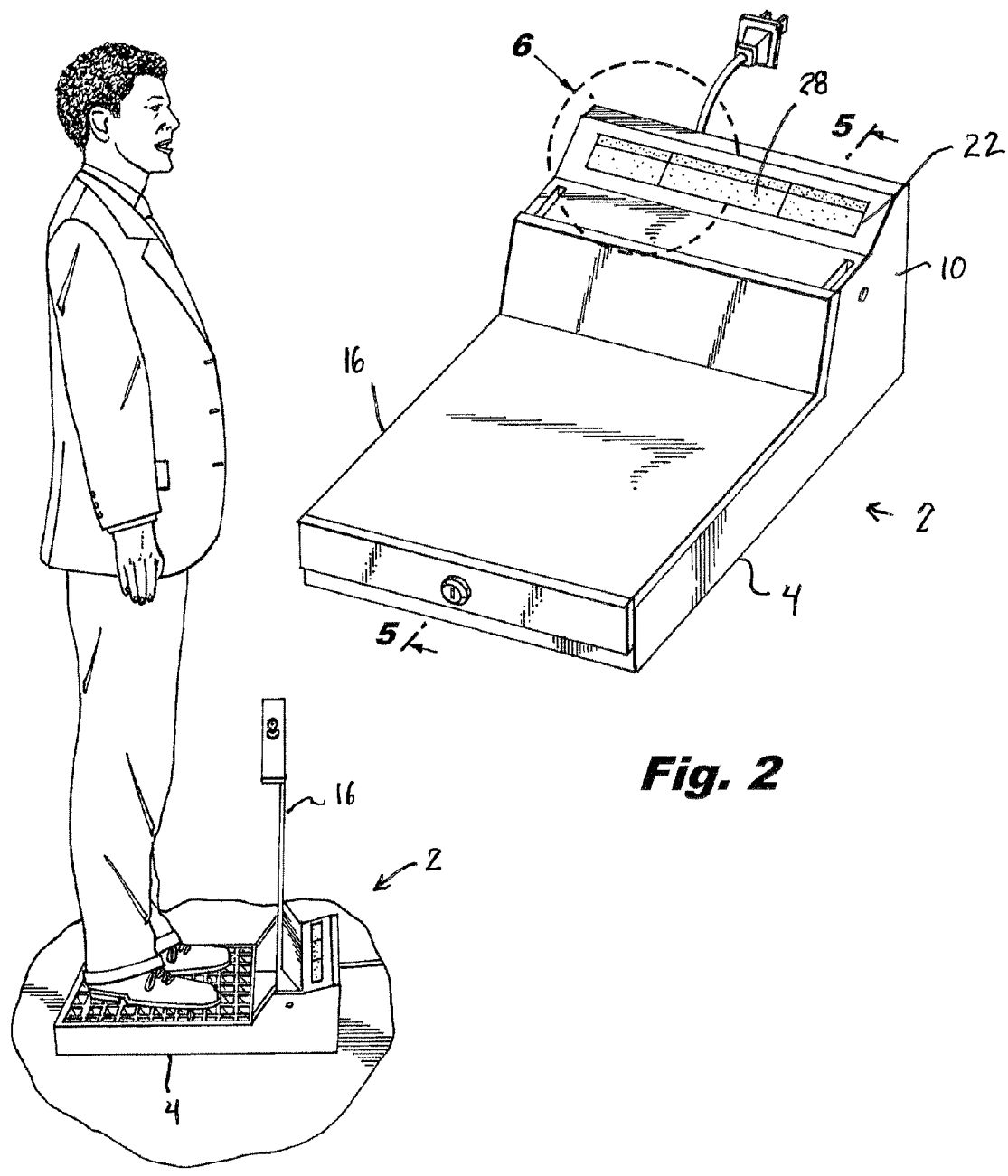
FIG. 1 is a side, perspective view of an embodiment of an apparatus for destroying pathogens in accordance with the present disclosure, illustrating a person standing thereon.
FIG. 2 is front, perspective view of the apparatus of FIG. 1, with a cover thereof in a closed configuration.
Figure 4:
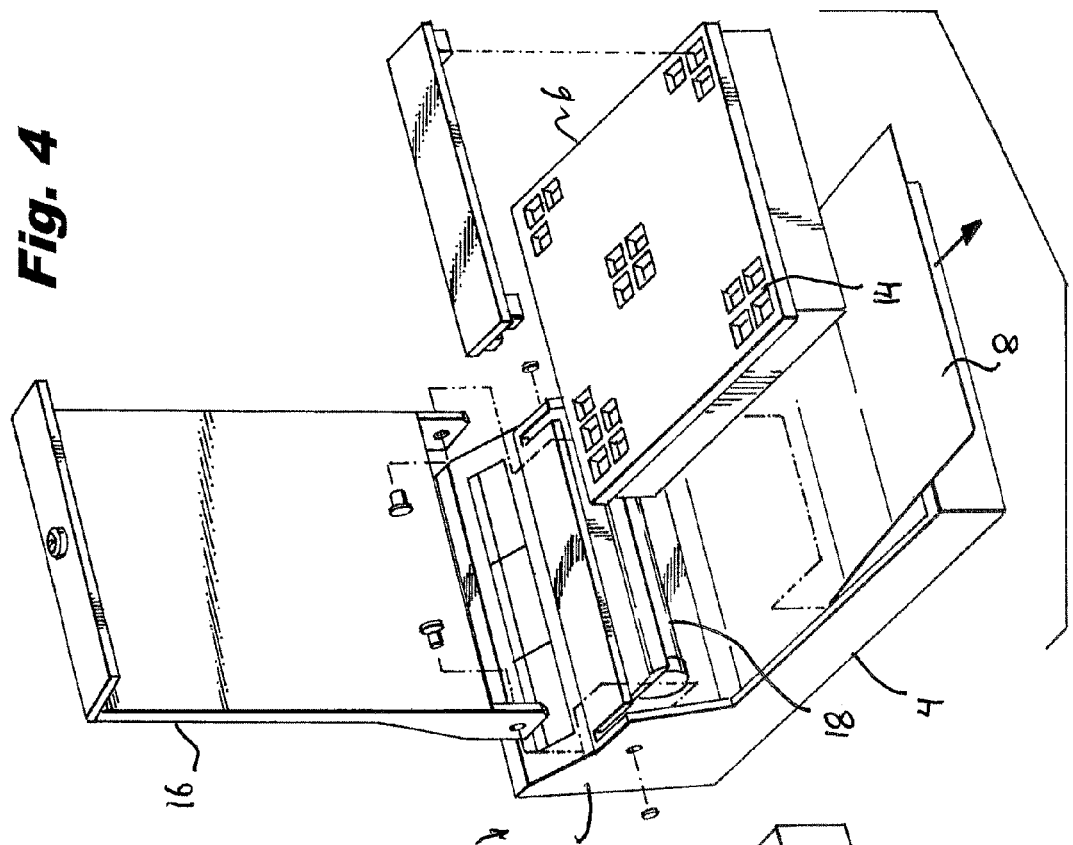
FIG. 4 is a partially exploded, perspective view of the apparatus of FIG. 1.
Figure 3:
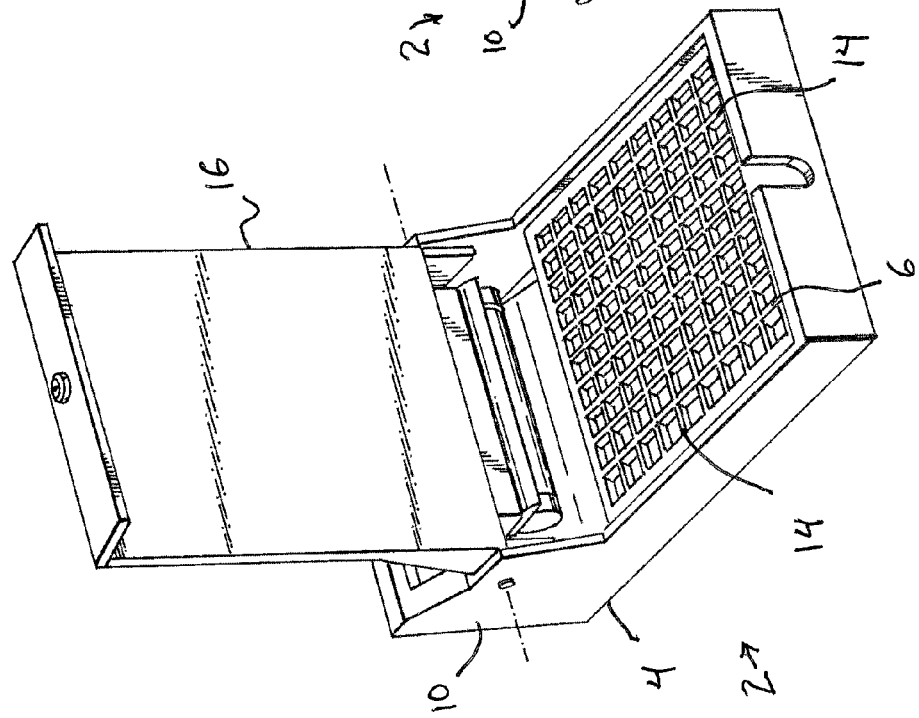
FIG. 3 is a perspective view of the apparatus of FIG. 1, with the cover in an opened configuration.

Embodiments of the presently disclosed apparatus for destroying pathogens are described in detail with reference to the drawings, in which like reference numerals designate identical or corresponding elements in each of the several views.

As used herein, the term "pathogen" includes, but is not limited to, viruses, bacteria (e.g., *Staphylococcus aureus*, MRSA, CDIF, VRE, *Pseudomonas aeruginosa* and *E. coli*), molds, spores, fungi, or the like.

Reference initially should be had to FIGS. 1-9 of the drawings. An apparatus, such as, for example, a sanitizer 2, for destroying pathogens associated with footwear or shoes is provided. The shoe sanitizer 2 of the present disclosure includes a housing 4 in the form of a five-sided box (i.e., front wall, rear wall, side walls and bottom wall) made of non-corrosive material. The approximate size of the housing 4 is 14 inches in length by 12 inches in width and 4 inches or less in height. It is contemplated that housing 4 may assume any suitable size and configuration. The frame of the housing 4 will have the strength to hold a platform, such as, for example, a grate 6 on which a person stands and support upwards of 800 pounds. The interior surface of the housing 4 is preferably reflective, and further includes a reflective sheet or tray 8, as will be described in greater detail below, which helps direct the ultraviolet light, and in particular, short-wavelength ultraviolet radiation ("UV-C light rays") to reach the shoe bottoms of a person standing thereon.

Sanitizer 2 includes a raised portion 10 extending from the housing 4 for receiving the electrical components and circuitry used in the shoe sanitizer 2. In particular, the electrical components and circuitry are situated in front of the "toe" area of a person's shoe 12. The height of the standing platform, i.e., where the grate 6 is located, is made as low as possible to make stepping on and off the sanitizer 2 easier.

The grate 6 is the platform situated on the top surface of the housing 4 that supports the user. The grate 6 is made from aluminum, and may additionally be coated with silver zeolite, in order to add an extra layer of sanitizing protection. In some embodiments, the grate 6 and/or other portions of the apparatus 2 may be fabricated from or coated with antimicrobial copper and/or Sharklet.

The grate 6 includes perpendicularly disposed bars 14 arranged in a grid-like manner. The bars 14 run longitudinally and transversely (i.e., widthwise) on the top surface of the housing 4. The transverse, or widthwise, running bars 14a are angled forwardly (i.e., towards the front or "toe" end of the sanitizer 2 in a direction from the top surface of the grate 6 to the bottom surface thereof), as can be seen in FIGS. 5 and 8-10 of the drawings. This particular angle at which the transverse bars 14a are disposed is provided to direct the UV-C light rays, emanating from an ultraviolet source of radiation, at an angle therethrough. In particular, the UV-C light rays are emitted from the source, and reflected by the reflective sheet or tray 8 toward the grate 6. Upon the UV-C light rays contacting the grate 6, the transverse bars 14a of the grate 6 alter the pathway of the UV-C light rays such that the UV-C light rays are angled relative to a plane defined by the grate 6 and contact the bottom soles of the shoes 12 worn by a person standing on the shoe sanitizer 2, while limiting the rays from being directed vertically upwardly and hitting objects beyond the immediate area of the grate 6. As such, a person standing on the sanitizer 2 and looking down at the grate 6 will not be able to directly view the light emanating from the ultraviolet light source and reflected by the reflective sheet or tray 8.

The dimensions of the crisscrossing of the longitudinal and transverse bars 14 including the grate 6 will be smaller at the back of the unit (where a person's heels of the shoes 12 will rest). Here, the grate 6 will define smaller openings to account for high-heeled shoes having narrow heels.

As can be seen from FIGS. 1-4 of the drawings, the sanitizer 2 of the present disclosure includes a cover or lid 16 that is pivotally attached to the housing 4 and which selectively covers and uncovers the grate 6. The lid 16 has the following exemplary benefits: when closed, it keeps debris from falling through the grate 6 and into the interior of the housing 4, which could affect the operation of the shoe sanitizer 2 and dirty or contaminate the reflective sheet or tray 8 therein; it provides an improved aesthetic appearance to the shoe sanitizer 2; it may be locked in a closed position, which will physically prevent a master switch forming part of the electrical circuitry of the sanitizer 2 from being turned on; and when opened, the underside of the lid 16 provides directions for the user on how to safely operate the shoe sanitizer 2, and such directions will be clearly visible to the user when standing on the grate 6 and with the lid 16 in its raised position.

The lid 16 flips open with the aid of counter springs. Once the lid 16 is raised about 6 inches, the springs help open the lid 16 to its fully raised position, which is at an obtuse angle of about 135 degrees with respect to the plane in which the grate 6 generally resides.

The lid 16 includes a small lip on the rear edge thereof, which allows the user to use their foot to raise the lid 16 so that they do not have to bend down and open the lid 16 with their hand.

As mentioned previously, there is a reflective sheet, or debris tray 8, situated within the interior of the housing 4 of the shoe sanitizer 2. The tray or sheet 8 is made from a plastic material covered with a reflective white polytetrafluoroethylene (PTFE) coating. It is contemplated that tray 8 may be fabricated from and/or coated with any suitable reflective material. The tray 8 has a slightly larger horizontal footprint than the grate 6. The tray 8 is set on an angle from a lower point near the base of the ultraviolet light source at the front "toe" side of the housing 4, rising to the top of the rear portion of the housing 4 at an angle of approximately 45 degrees (see FIGS. 8-10 of the drawings). In some embodiments, the tray 8 may be curved. It is contemplated that sanitizer 2 may include a hood or fence (not shown) that extends from portions of or the entire periphery of housing 4. The fence is fabricated from or coated with a non-reflective material to absorb ultraviolet light that passes adjacent the shoes of a user thereby preventing the ultraviolet light from contacting objects outside of the vicinity of sanitizer 2.

The reflective tray 8 serves at least two purposes. It reflects light from the ultraviolet light source onto the bottom of the shoes 12. Additionally, it catches debris which falls from the shoes 12 when a user is standing on the grate 6.

The tray 8 can slide out from the housing 4 and be cleaned to remove any debris that has dropped down onto it from the user's shoes 12.

The tray 8 includes an upturned lip (not shown) that surrounds the central planar portion of the tray 8 to keep debris from spilling out when the tray 8 is being removed from the housing 4 for cleaning.

As a safety precaution, the shoe sanitizer 2 of the present disclosure may be configured not to operate without the tray 8 being properly installed within the housing 4. A switch (not shown) within the interior of the housing 4 engages the tray 8 when the tray 8 is properly received by the housing 4. Upon the tray 8 being properly received within the housing 4, the switch will be activated to allow the electric circuitry and ultraviolet light source of the shoe sanitizer 2 to operate.

The ultraviolet light source is preferably an ultraviolet bulb 18 that emits UV-C light, which has been proven to kill pathogens. In some embodiments, the UV-C light has a wavelength of about 254 nm. The kill rate of the pathogens is based on the intensity and duration of the UV-C light shining on the shoe soles. The ultraviolet light bulb 18 is positioned at the forward or "toe" end of the housing 4 under the raised portion 10 thereof and below the grate 6, and its activation and intensity are controlled by the electrical circuits. The ultraviolet light bulb 18 is chosen so that it will physically fit inside the housing 4 of the shoe sanitizer 2 and allow the least amount of time required to sanitize the wearer's shoes 12 and to meet all safety concerns, including not being overly intensive. Light emitted by the bulb 18 contacts the reflective surface of the tray 8, from which the light is reflected through the angled bars 14a of the grate 6 and onto the soles of a person's shoes 12 standing on the grate 6. In some embodiments, the ultraviolet bulb 18 may have an elongated, cylindrical configuration and may extend from a left sidewall to a right sidewall of the housing 4.

Sanitizer 2 includes a reflector 20 situated behind the ultraviolet bulb 18 configured to aid in directing the UV-C light emanating from the bulb 18 to contact the soles of the wearer's shoes 12. The reflector 20 is parabolic in shape such that the UV-C light emanating from the bulb 18 will be directed onto the reflective tray 8. In some embodiments, the reflector 20 may assume a variety of shapes, such as, for example, oblong, arcuate, square, rectangular triangular, or the like. The reflector 20 is made of a durable reflective material, and is positioned at an optimal angle in order to direct light onto the reflective tray 8 and then onto the shoe soles placed on the grate 6.

In order to help the user with the operation of the shoe sanitizer 2 of the present disclosure, a communication display board 22, such as shown in FIGS. 6 and 7, is mounted on the housing 4 at the raised portion 10 thereof. The communication display board 22 will indicate the status of the operation of the shoe sanitizer 2, along with displays of warnings and instructions, and sounds emitted by a transducer or loudspeaker 24. An on/off power switch 26 is also preferably included on the communication display board 22. During a sanitizing operation, the display board 22 will count down the remaining time until the user's shoes 12 are fully sanitized, and the time remaining will be displayed for the user to view. The communication display board 22 includes either liquid crystal displays (LCDs) 28 or light emitting diode (LED) displays 28.

As a further layer of safety, and to ensure that small children will be prevented from using the shoe sanitizer 2 of the present disclosure, one or more strain gauges are mounted on the housing 4 on the bottom side thereof. The housing 4, on its bottom side, may include four short legs 30 situated in the four corners of the housing 4, and each strain gauge may be mounted in or on a respective leg 30. The strain gauge or gauges will sense the weight of the person standing on the grate 6 of the shoe sanitizer 2, and will output electrical signals to the circuit of the sanitizer 2, the output signals from the strain gauges being indicative of the weight of the person standing on the shoe sanitizer 2. In response to the output signals from the strain gauges, the electrical circuit will determine whether the weight of the person standing on the shoe sanitizer 2 is below a predetermined threshold value, such as 70 pounds, and will not activate the ultraviolet light source if the weight of the person is below the predetermined threshold value. This will ensure that, even if the lid 16 is raised, children will not be able to activate the shoe sanitizer 2.

The operating process of the shoe sanitizer 2 of the present disclosure is illustrated by the chart shown below:

| Sanitizer Operating Process | | |
|---|---|---|
| Physical Process | Electronic Process | Display/Sound |
| 1 Power cord is plugged in | Power supply to microprocessor | Power light - green |
| 2 Cover is opened | Cover switch - On | |
| 3 Master Switch - Turned On | Master switch - On | Ready light - green Audible Alarm |
| 4 (Automatically starts from previous) | Tray switch (Reflective debris tray installed correctly) | Tray Light Correct - green Incorrect - red |
| 5 (Automatically starts from previous) | Strain gauge (70 lbs min.) | Weight Light Under Min - Red |
| 6 Stand on sanitizer | Strain gauge (70 lbs min.) | Weight Light Over Min - Green |
| 7 (Automatically starts from previous) | Countdown timer starts (3 seconds) | Timer Light Yellow Flashing Audible Alarm |
| 8 (Automatically starts from previous) | Sanitation process starts; UVc Blubs turn on | Sanitizing Lights Yellow lights change to Green as the process get closer to completion |
| 9 (Automatically starts from previous) | Timer turns off | Audible Alarm Sanitizing Lights Flash then go off |
| 10 Note: | Resets to step 3 If process 4 or 5 turns false during the Sanitizing Process the process will stop and reset to step 3. | |

In Step 1, the power cord is plugged into an AC wall outlet, and power is supplied to the electrical circuit, which includes a microprocessor. A green power light is displayed on the LCD or LED display 28.

In Step 2, the user raises the lid or cover 16. This turns the cover switch on to activate further circuits in the shoe sanitizer 2.

In Step 3, the user turns on the master switch (on/off power switch 26). The activation of the master switch is detected by the electrical circuit and the microprocessor thereof, and a "ready" light, which is green, is illuminated, and an audible alarm is sounded.

In Step 4, the electrical circuit of the shoe sanitizer 2 checks to see if the tray switch is in a particular state, indicating that the reflective debris tray 8 is installed correctly. A tray light will illuminate either green, to indicate that the tray 8 is installed correctly, or red, to indicate that the tray 8 is not correctly installed. If the tray light is red, the user will have to adjust the reflective tray 8 to make sure that it is properly installed within the interior of the housing 4.

In Step 5, the electrical circuit of the shoe sanitizer 2 will now receive the output signals of the strain gauge or gauges. The person is instructed to stand on the sanitizer 2, and the strain gauges will output signals to the microprocessor, which will determine whether the weight of the person standing on the sanitizer 2 is below the predetermined threshold value. As stated previously, the preferred threshold value corresponds to a weight of 70 pounds. If the strain gauge or gauges sense the person's weight as being less than 70 pounds, then a weight light illuminates in red, indicating that the person's weight is under the required minimum weight to operate the shoe sanitizer 2. If, however, the strain gauge or gauges signal the microprocessor that the person's weight is equal to or greater than the predetermined 70 pound minimum threshold value, then the weight light will illuminate in green, indicating that the person's weight is over the minimum weight required to operate the shoe sanitizer 2 (see Step 6).

In Step 7, the electrical circuit of the shoe sanitizer 2 starts a countdown timer for a predetermined period of time, which is preferably about three seconds. A timer light illuminates in yellow and is preferably flashing, and an audible alarm sounds.

In Step 8, the electrical circuit of the shoe sanitizer 2 starts the sanitization process. The ultraviolet light bulb 18 is turned on, and light is emitted from the bulb 18 and reflected off the tray 8 onto the soles of the shoes 12 of the user standing on the grate 6. One or more sanitizing display lights are illuminated, first in yellow and then changing to green as the sanitizing process approaches completion. A timer determines how long the sanitizing process should be.

In Step 9, the sanitizing process timer turns off, and causes the electrical circuit to sound an audible alarm and flash the sanitizing display lights to indicate that the sanitizing process has been completed. The sanitizing display lights will flash, and then will go off.

In Step 10, after the completion of the sanitizing process, the operation of the shoe sanitizer 2 will return to Step 3, described above and shown in the chart.

It should be noted that, in Steps 4 or 5 of the sanitizer operating process, if the tray switch indicates that the reflective debris tray 8 is not correctly installed, or that the strain gauge or gauges measure the person's weight as being below the minimum threshold weight (e.g., 70 pounds), then the operating process will stop and reset to Step 3.

Figure 10:
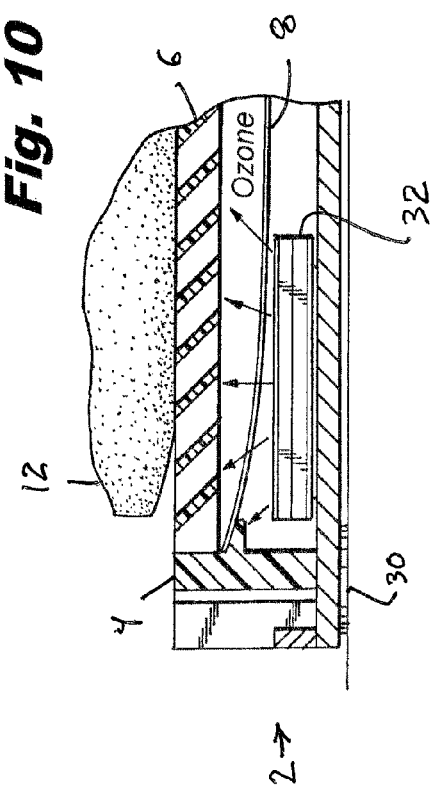
FIG. 10 is a detailed cross-sectional view of a portion of an apparatus for destroying pathogens constructed in accordance with another embodiment of the present disclosure.
Figure 9:
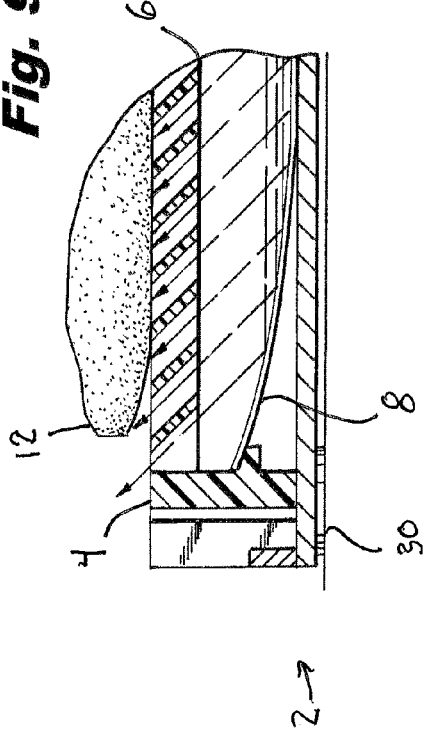
FIG. 9 is a detailed, cross-sectional view of a portion of the apparatus shown encircled by the broken line labeled 9 in FIG. 8.

FIG. 10 illustrates an alternative embodiment of the shoe sanitizer 2 of the present disclosure. In this embodiment, an ozone generator 32 may be mounted within the interior of the housing 4. The ozone generator 32 is configured to emit an ozone gas when energized by the electrical circuit of the shoe sanitizer 2. In the embodiment shown in FIG. 10, the ozone generator 32 is shown being mounted below the reflective debris tray 8 and in proximity to, and more preferably in alignment with, a position under the grate 6 where it is anticipated that the shoes 12 of a person standing on the grate 6 will be located. The reflective debris tray 8 may be perforated to allow ozone gas emitted by the ozone generator 32 to pass therethrough and to contact the bottom of the person's shoes 12. As is well known, ozone gas is effective in killing bacteria and pathogens. Accordingly, in this particular embodiment, not only is UV-C ultraviolet light used, but also ozone gas is used, to sanitize the shoes 12 of a person standing on the sanitizer 2 of the present disclosure.

Figure 8:
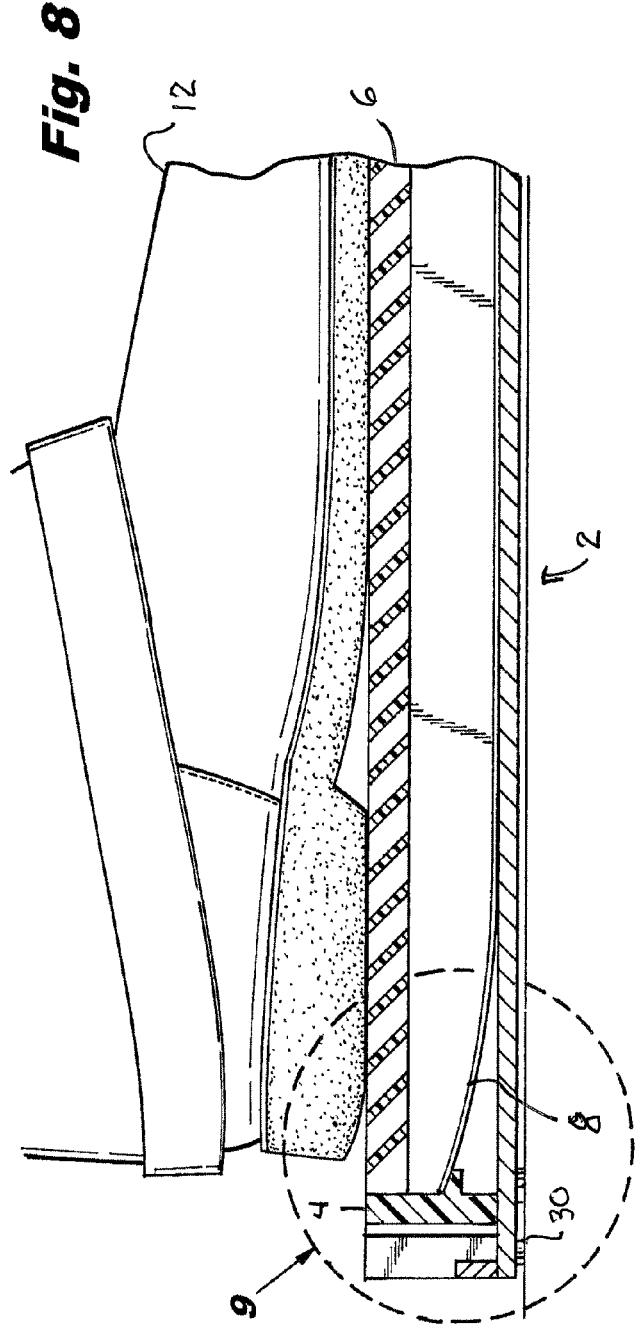
FIG. 8 is a partial, cross-sectional view of the apparatus of the present disclosure, illustrating a person standing thereon.
Figure 11:
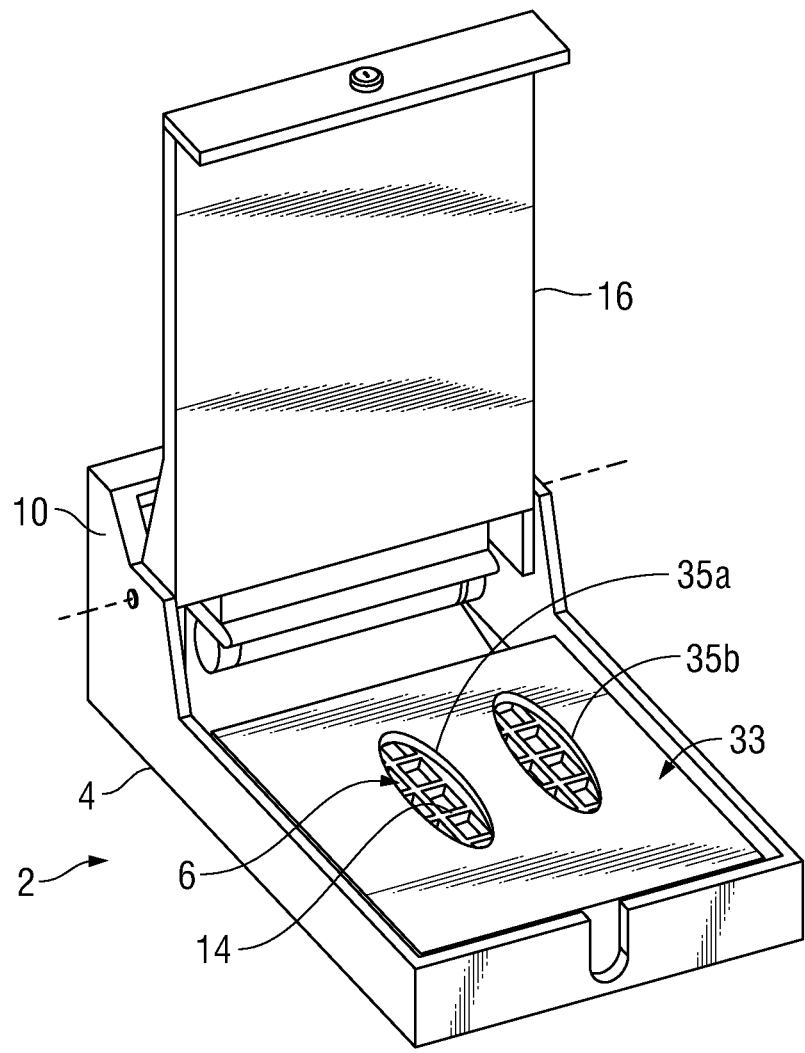
FIG. 11 is a perspective view of the apparatus of FIG. 1 including a mat disposed on a platform of the apparatus.

With reference to FIG. 11, the sanitizer 2 includes a mat, such as, for example, a shoe mat 33, which is configured to be removably positioned on the top surface of the grate 6. In some embodiments, the mat 33 may be fixed to the top surface of the grate 6. The mat 33 has cutouts 35a, 35b formed through the thickness thereof. The cutouts 35a, 35b have an oblong configuration dimensioned to receive footwear (e.g., shoes, sneakers, boots, etc.). In some embodiments, the cutouts 35a, 35b may generally be in the shape of a user's shoes 12 (FIG. 8). The cutouts 35a, 35b may be of a general size, such as a men's size 11, or may be custom cut by the user to closely fit the size of the user's shoe soles. Accordingly, a plurality of mats 33 may be provided, each having a different sized cutout corresponding to a shoe size of a user. The mat 33 is provided as an added layer of safety. Users can place the mat 33 on the top surface of the grate 6, and stand on the mat 33 with their shoes 12 (FIG. 8) directly received by the cutouts 35a, 35b in the mat 33. Thus, the mat 33 will allow the ultraviolet light to contact the bottom of the shoes 12 received by the cutouts 35a, 35b, but will block the ultraviolet light from passing through portions of the grate 6 that are covered by the mat 33.

Figure 12:
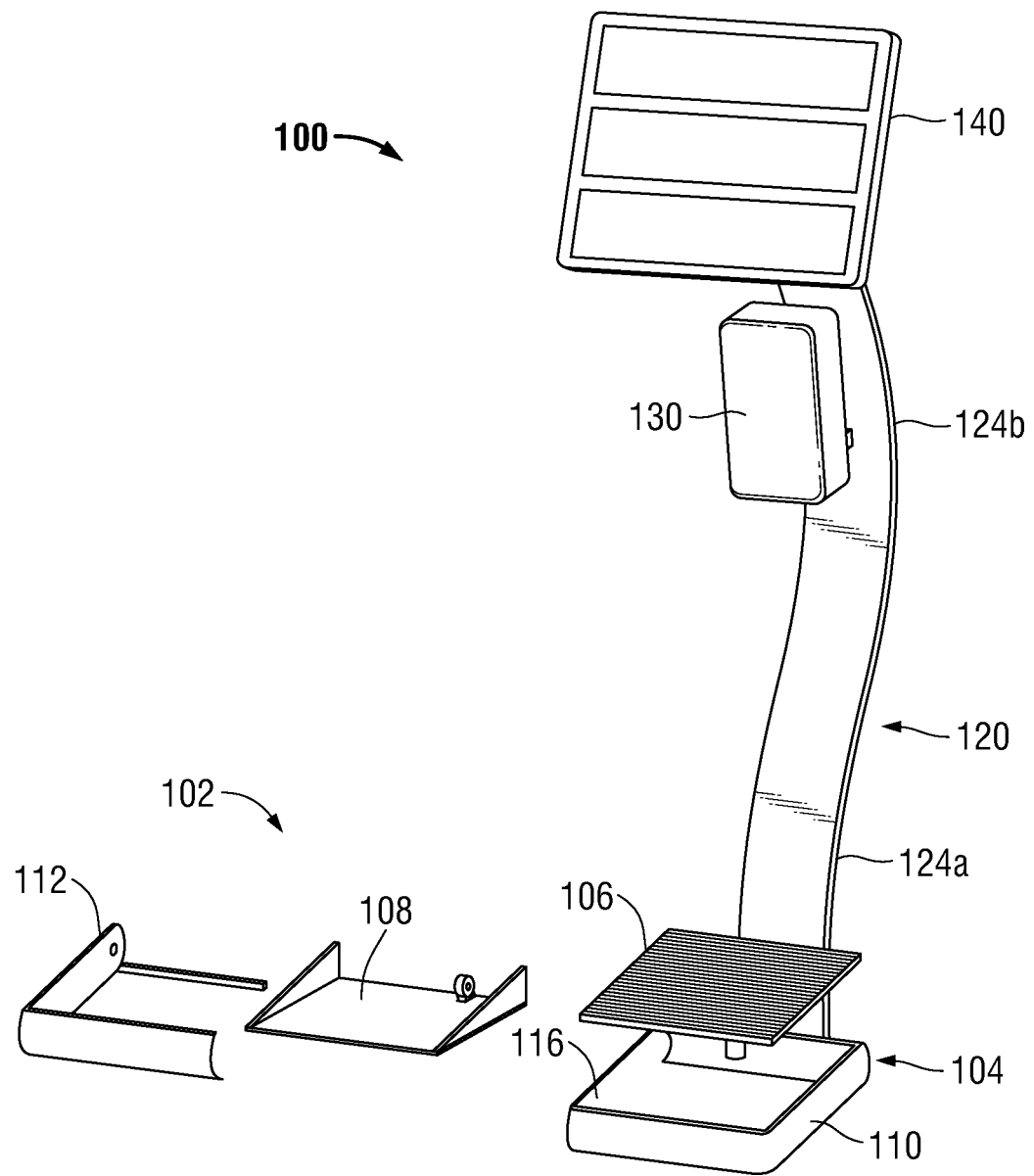
FIG. 12 is a perspective view, with parts separated, of a sanitizing station for destroying pathogens.
Figure 13:
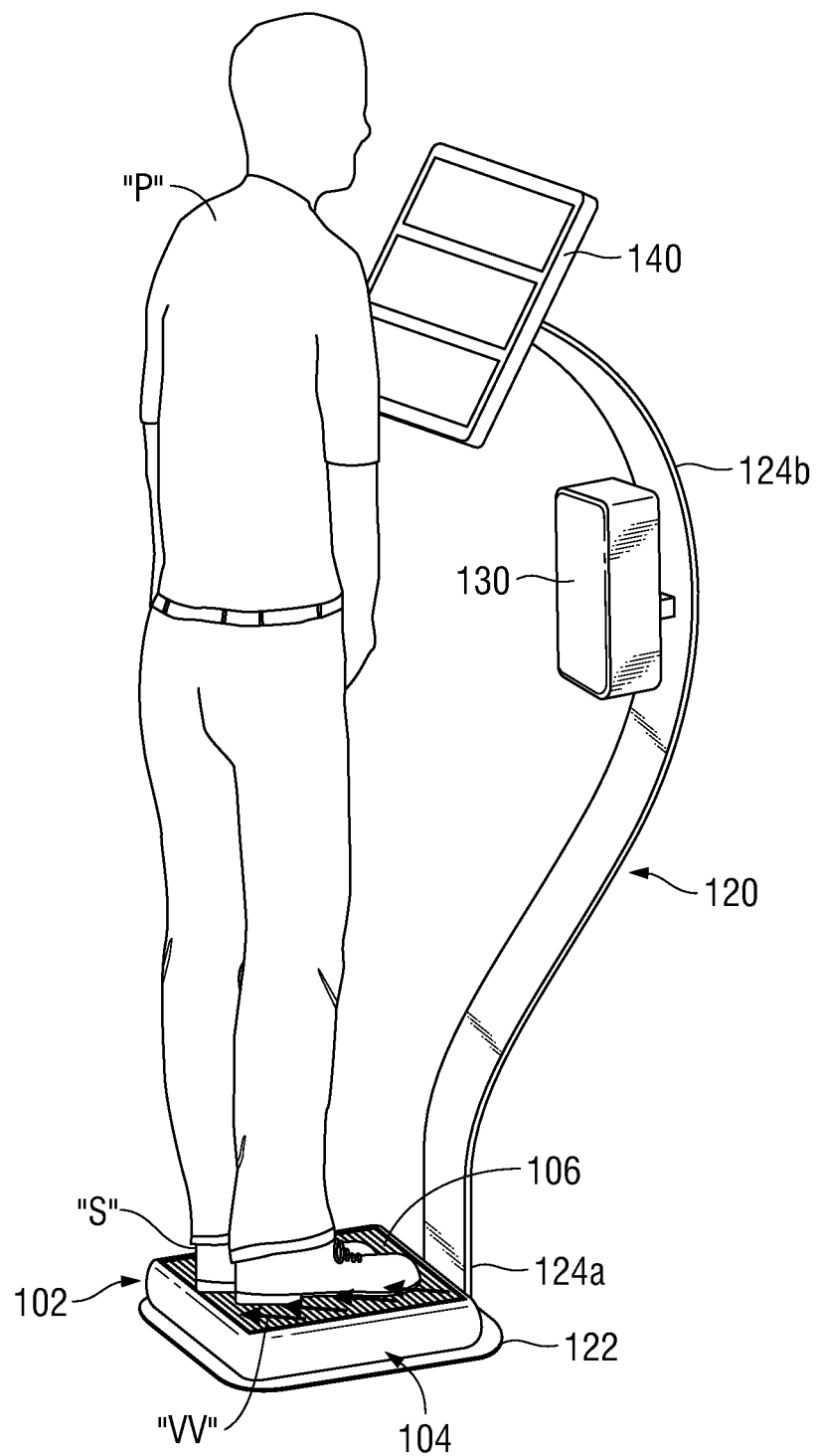
FIG. 13 is a perspective view of the sanitizing station of FIG. 12 illustrating a person standing thereon.

With reference to FIGS. 12 and 13, an embodiment of a sanitizing station is provided, which is referenced generally as 100. The sanitizing station 100 includes an apparatus 102 for destroying pathogens, similar to shoe sanitizer 2 described above, a stanchion 120 extending from the apparatus 102, a hand sanitizing apparatus 130, and a display 140. The apparatus 102 includes a housing 104, a platform 106, similar to grate 6 described above, a reflective tray 108, similar to reflective tray 8 described above, and a source of ultraviolet light (not shown), similar to the ultraviolet bulb 18 described above.

The housing 104 includes a main body 110 and a sliding member 112. The main body 110 defines a cavity 114 for receiving the components of the apparatus 102. The platform 106 is configured to be supported on the main body 110 to cover the cavity 114. The main body 110 defines a side opening 116 in communication with the cavity 114 and configured for removably receiving the sliding member 112. The sliding member 112 covers the side opening 116 such that the cavity 114 is enclosed upon assembling both the sliding member 112 and the platform 106 to the main body 110 of the housing 104. Upon detaching the removable sliding member 112 from the main body 110, components, e.g., the reflective tray 118 and the source of UV-C light, can be removed from the main body 110 by moving them out of the cavity 114 through the side opening 116.

The stanchion 120 of the station 100 has a base 122 (FIG. 13) for supporting the housing 104, and a first end portion 124a and a second end portion 124b. The stanchion 120 has an undulating shape. In some embodiments, the stanchion 120 may assume a variety of shapes, such as, for example, arcuate, v-shaped, linear, or the like. The first end portion 124a is attached to a front end of the base 122 and extends perpendicularly therefrom. In some embodiments, the stanchion 120 may not have a base, and instead, be directly coupled to a front end of the housing 104. The second end portion 124b of the stanchion 120 has the hand sanitizing apparatus 130 attached thereto. In some embodiments, the hand sanitizing apparatus 130 may be in the form of a hand sanitizer dispenser.

The second end portion 124b of the stanchion 120 also has the display 140 attached thereto, which may be disposed above the hand sanitizing apparatus 130. The display 140 is electrically connected (wirelessly or via wires) to a microprocessor and/or circuitry (not shown) disposed within the housing 104 such that information can be communicated between the display 140 and the housing 104. The display 140 may be an LCD or LED display that displays information related to the progress of the sanitizing process. For example, the display 140 may display a countdown for the amount of time a person "P" standing on the platform 106 needs to remain until the sanitizing process is completed. Further, the display 140 may be a touchscreen that allows the person "P" to select when the sanitizing process is to begin and/or to input certain information, e.g., size of the footwear to be sanitized, the type of footwear, or the level of sanitizing required (e.g., a killing of only selected types of pathogens), such that the sanitizing process can be tailored to the person "P."

In operation, a person "P" wearing footwear, e.g., shoes "S," positions their feet on the platform 106 of the housing 104. Using the display 140, the person "P" may input parameters (e.g., size of the footwear, type of the footwear, physical setting in which the footwear will be used (e.g., home, hospital, etc.)) and then select for the sanitizing process to begin. In addition, the hand sanitizing apparatus 130 may also be actuated to dispense hand sanitizer. Upon activating the sanitizing process, ultraviolet light "UV," indicated by arrows "UV" in FIG. 13, is emitted by the ultraviolet light source (not shown) and contacts the reflective tray 108 thereby reflecting the ultraviolet light "UV" up and through the platform 106 at an angle. The ultraviolet light "UV" makes contact with a bottom of the shoes "S" at an acute angle relative to the bottom of the shoes "S." By passing the ultraviolet light "UV" through the platform 106 at an angle, the ultraviolet light "UV" destroys pathogens associated with the footwear without making contact with the body of person "P."

Example 1

An embodiment of the shoe sanitizer of the present disclosure was used to determine its efficacy in destroying *clostridium difficile*—spore form (ATCC 43598). The test was conducted at room temperature. Two pieces of rubber were provided, one of which acting as the test carrier and the other as the control carrier. A bottom surface of each rubber piece was inoculated with *clostridium difficile* in the following amount: $4\times10^5$ ($5.60\,\text{Log}_{10}$) CFU/carrier.

The shoe sanitizer was turned on and allowed to run for one (1) minute. The test rubber piece was positioned on the middle-right area of the platform with the inoculated bottom surface in contact with the platform. After (15) seconds of being exposed to ultraviolet light, the test rubber piece was removed and tested to determine the survival of *clostridium difficile* compared to the control rubber piece. Provided below are the results of the test.

Carrier Population Control Results—Number of Survivors: $4\times10^5$ ($5.60\,\text{Log}_{10}$) CFU/carrier. As expected, no change in the amount of *clostridium difficile* occurred in the control test.

Carrier Population Test Results—Number of Survivors: $2.8\times10^4$ ($4.45\,\text{Log}_{10}$) CFU/carrier. Accordingly, the shoe sanitizer reduced the amount of *clostridium difficile* in the test rubber piece by 93.0% ($1.15\,\text{Log}_{10}$).

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An apparatus for destroying pathogens, comprising:
   a housing;
   a platform supported on the housing and configured to permit passage of ultraviolet light at an angle therethrough;
   a reflective tray disposed within the housing; and
   a source of ultraviolet light disposed adjacent the reflective tray such that the reflective tray directs ultraviolet light emitted by the source of ultraviolet light through the platform, said platform further configured to block all ultraviolet light from passing through the platform along an axis parallel to a transverse axis defined by the platform.

2. The apparatus according to claim 1, wherein the platform has a plurality of spaced apart transverse bars.

3. The apparatus according to claim 2, where each bar of the plurality of spaced apart transverse bars is angled relative to the transverse axis defined by the platform such that the ultraviolet light passes through spaces defined between adjacent bars at a non-perpendicular angle relative to a plane defined by the platform.

4. The apparatus according to claim 3, wherein each bar of the plurality of spaced apart transverse bars is angled in a direction from a top surface of the platform to a bottom surface of the platform such that the ultraviolet light is directed away from the front end of the housing.

5. The apparatus according to claim 3, wherein the spaces each define an axis extending at an angle oriented away from the front end of the housing, the angle being between 1 and 90 degrees relative to the plane of the platform.

6. The apparatus according to claim 2, wherein the platform further includes a plurality of spaced apart longitudinal bars in a crisscrossing arrangement with the plurality of spaced apart transverse bars.

7. The apparatus according to claim 6, wherein the plurality of spaced apart transverse bars and the plurality of spaced apart longitudinal bars together define a plurality of openings, openings of the plurality of openings located adjacent a rear end of the platform being smaller in dimension than openings of the plurality of openings located adjacent a front end of the platform.

8. The apparatus according to claim 1, wherein the platform is fabricated from aluminum.

9. The apparatus according to claim 1, further comprising a cover attached to the housing and configured to selectively cover the platform.

10. The apparatus according to claim 1, wherein the reflective tray is fabricated from a plastic material having a reflective white polytetrafluoroethylene coating.

11. The apparatus according to claim 1, wherein the reflective tray has a first end disposed adjacent the source of ultraviolet light and a second end disposed adjacent a rear end of the housing, the second end of the reflective tray being angled relative to the first end in a direction toward the platform.

12. The apparatus according to claim 1, wherein the source of ultraviolet light is an ultraviolet bulb that emits short-wavelength ultraviolet radiation, the ultraviolet bulb being disposed within the housing at a front end of the housing.

13. The apparatus according to claim 12, further comprising a reflector disposed on the ultraviolet light bulb and configured to direct ultraviolet light emitted by the ultraviolet bulb toward the reflective tray.

14. The apparatus according to claim 1, further comprising a mat positionable on the platform, wherein the mat has a pair of cutouts formed through a thickness thereof that have an oblong configuration, the mat being configured to allow passage of ultraviolet light only through the pair of cutouts.

15. The apparatus according to claim 1, further comprising at least one strain gauge configured to sense a weight of a person standing on the platform.

16. The apparatus according to claim 1, further comprising an ozone generator disposed within the housing between a base of the housing and the reflective tray.

17. The apparatus according to claim 16, wherein the reflective tray is perforated to allow passage of ozone gas emitted by the ozone generator.

18. A method of sanitizing footwear, comprising:
providing an apparatus for destroying pathogens, the apparatus including:
a housing;
a platform supported on the housing and configured to permit passage of ultraviolet light at an angle therethrough;
a reflective tray disposed within the housing; and
a source of ultraviolet light disposed adjacent the reflective tray, said platform further configured to block all ultraviolet light from passing through the platform along an axis parallel to a transverse axis defined by the platform;
positioning footwear on the platform; and
emitting, from the source of ultraviolet light, ultraviolet light, wherein the ultraviolet light contacts the reflective tray thereby directing the ultraviolet light through the platform, at an angle, and into contact with the footwear.

19. The method according to claim 18, further comprising passing the ultraviolet light, at a non-perpendicular angle relative to a plane defined by the platform, through spaces defined through the platform.

20. The method according to claim 18, further comprising directing the ultraviolet light away from a front end of the housing.

21. An apparatus for destroying pathogens, comprising:
a housing;
a platform supported on the housing and configured to permit passage of ultraviolet light at an angle therethrough;
a reflective tray disposed within the housing; and
a source of ultraviolet light disposed adjacent the reflective tray such that the reflective tray directs ultraviolet light emitted by the source of ultraviolet light through the platform;
wherein the platform has a plurality of spaced apart transverse bars;
wherein the platform further includes a plurality of spaced apart longitudinal bars in a crisscrossing arrangement with the plurality of spaced apart transverse bars; and
wherein the plurality of spaced apart transverse bars and the plurality of spaced apart longitudinal bars together define a plurality of openings, openings of the plurality of openings located adjacent a rear end of the platform being smaller in dimension than openings of the plurality of openings located adjacent a front end of the platform.

22. An apparatus for destroying pathogens, comprising:
a housing;
a platform supported on the housing and having a plurality of rectangular transverse bars, each of said rectangular transverse bars being parallel to at least one adjacent rectangular transverse bar, said platform configured to permit passage of ultraviolet light at an angle therethrough;
a reflective tray disposed within the housing; and
a source of ultraviolet light disposed adjacent the reflective tray such that the reflective tray directs ultraviolet light emitted by the source of ultraviolet light through the platform, said platform further configured to block ultraviolet light from passing through the platform along an axis parallel to a transverse axis defined by the platform.

23. The apparatus according to claim 22, where each bar of the plurality of spaced apart rectangular transverse bars is angled relative to the transverse axis defined by the platform such that the ultraviolet light passes through spaces defined between adjacent bars at a non-perpendicular angle relative to a plane defined by the platform.

24. The apparatus according to claim 23, wherein each bar of the plurality of spaced apart rectangular transverse bars is angled in a direction from a top surface of the platform to a bottom surface of the platform such that the ultraviolet light is directed away from the front end of the housing.

25. The apparatus according to claim 23, wherein the spaces each define an axis extending at an angle oriented away from the front end of the housing, the angle being between 1 and 90 degrees relative to the plane of the platform.

26. The apparatus according to claim 22, wherein the platform further includes a plurality of spaced apart longitudinal bars in a crisscrossing arrangement with the plurality of spaced apart rectangular transverse bars.

27. The apparatus according to claim 26, wherein the plurality of spaced apart rectangular transverse bars and the plurality of spaced apart longitudinal bars together define a plurality of openings, openings of the plurality of openings located adjacent a rear end of the platform being smaller in dimension than openings of the plurality of openings located adjacent a front end of the platform.

28. The apparatus according to claim 22, wherein the platform is fabricated from aluminum.

29. The apparatus according to claim 22, further comprising a cover attached to the housing and configured to selectively cover the platform.

30. The apparatus according to claim 22, wherein the reflective tray is fabricated from a plastic material having a reflective white polytetrafluoroethylene coating.

31. The apparatus according to claim 22, wherein the reflective tray has a first end disposed adjacent the source of ultraviolet light and a second end disposed adjacent a rear end of the housing, the second end of the reflective tray being angled relative to the first end in a direction toward the platform.

32. The apparatus according to claim 22, wherein the source of ultraviolet light is an ultraviolet bulb that emits short-wavelength ultraviolet radiation, the ultraviolet bulb being disposed within the housing at a front end of the housing.

33. The apparatus according to claim 32, further comprising a reflector disposed on the ultraviolet light bulb and configured to direct ultraviolet light emitted by the ultraviolet bulb toward the reflective tray.

34. The apparatus according to claim 22, further comprising a mat positionable on the platform, wherein the mat has a pair of cutouts formed through a thickness thereof that have an oblong configuration, the mat being configured to allow passage of ultraviolet light only through the pair of cutouts.

35. The apparatus according to claim 22, further comprising at least one strain gauge configured to sense a weight of a person standing on the platform.

36. The apparatus according to claim 22, further comprising an ozone generator disposed within the housing between a base of the housing and the reflective tray.

37. The apparatus according to claim 36, wherein the reflective tray is perforated to allow passage of ozone gas emitted by the ozone generator.

* * * * *